United States Patent [19]  [11] 4,254,147
Cavazza  [45] Mar. 3, 1981

[54] PHARMACEUTICAL COMPOSITION FOR TOTAL PARENTERAL NUTRITION

[76] Inventor: Claudio Cavazza, 35, Via Marocco, 00144 Rome, Italy

[21] Appl. No.: 41,645

[22] Filed: May 23, 1979

[30] Foreign Application Priority Data

May 25, 1978 [IT] Italy .............................. 49534 A/78

[51] Int. Cl.³ .......................................... A61K 31/205
[52] U.S. Cl. ..................................................... 424/316
[58] Field of Search ......................................... 421/316

[56] References Cited

U.S. PATENT DOCUMENTS 3,793,450  2/1974  Schnell .................................. 424/343
3,810,994  5/1974  Wiegand ............................... 424/316

Primary Examiner—Stanley J. Friedman
Attorney, Agent, or Firm—Jacobs & Jacobs

[57] ABSTRACT

A composition for total or supplemental parenteral nutrition of patients in need thereof for the treatment of shock and trauma, is disclosed. The composition comprises a therapeutically effective amount of triglycerides and an amount of carnitine or a pharmaceutically acceptable salt thereof sufficient to increase free fatty acid oxidation.

11 Claims, No Drawings

PHARMACEUTICAL COMPOSITION FOR TOTAL PARENTERAL NUTRITION

BACKGROUND OF THE INVENTION

1. Field of the Invention

The present invention relates to a novel pharmaceutical composition for total or supplemental parenteral nutrition of patients in need thereof for treatment of shock and other trauma.

More particularly, the present invention relates to a novel composition for use in total or supplemental intravenous nutrition of patients in need thereof, such composition comprising a therapeutically effective amount of triglycerides. The present invention also relates to a therapeutical method of increasing the efficiency of triglyceride administration to patients in need thereof because of their condition of shock and trauma.

2. Description of the Prior Art

Up until recently, total parenteral nutrition was limited to the use of carbohydrates and protein hydrolysates, whereas intravenous administration of fats as caloric source was actually avoided in spite of its acknowledged utility based on the long-standing knowledge that several tissues, particularly the muscular tissue and the myocardium, utilize fatty acids as preferential energy substrate. Consequently, intravenous administration of exogenous fats would result in markedly beneficial effects in all those clinical situations wherein unbalanced conditions of some metabolic systems may occur.

One of these systems is for instance the adjustment system of the lipolysis whose role is that of furnishing suitable material to the tissues which utilize fatty acids and ketone bodies as energy source.

A second system, more closely related to the phenomena of the mitochondrial respiration, is the system wherein the carnitine-acetyl carnitine transferase complex plays an essential role. This complex is strictly related to the activity of ATP mitchrondial translocase and acts so as to allow the passage of the activated, long-chain free fatty acids through the mitochondrial membrane to take place and their attendant conveyance to the bate-oxidation sites.

The consequence brought about by the alterations of the above-mentioned systems is the intracellular accumulation of long-chain fatty acids which, therefore, cannot be properly utilized. The muscular cells are thus deprived of an energy substrate of the utmost importance and muscular proteolysis is thereby enhanced with attendant loss of branched-chain amino acids which are utilized by the muscular tissues for energy purposes. This impaired free fatty acid utilization causes the blockage of several enzyme systems of the mitochondrial walls and the onset of cardiac rhythm disturbances.

More recently, administration of triglycerides to patients affected by conditions of shock and trauma has become a problem of major concern and after extensive experimentation and researches lipid packs in the form of an intravenous emulsion of fats and oils have been developed and become commercially available. As an instance of useful lipid pack, Intralipid (marketed by Cutter Laboratoires, Berkeley, California) can be cited. Intralipid is made up of 10% soybean oil (a mixture of the glycerides of oleic, linolic, palmitic, stearic and linolenic acids), 1.2 egg yolk phospholipids, 2.25% glycerin, the balance being water for injection, sufficient sodium hydroxide being added to adjust the pH to 5.5–9.0.

Exogenous triglycerides of the intravenous fate emulsion are intended to be hydrolyzed in the body by lipase with attendant formation of glycerol and fatty acids. These latter should in turn undergo progressive oxidation.

SUMMARY OF THE INVENTION

It has been found however that the administration of lipid packs to patients in need of exogenous triglycerides frequently does not lead to therapeutically satisfactory results because of the sharply reduced clearance of triglycerides and free fatty acids by patients in shock and trauma, particularly by intensively catobolic patients (such as, e.g. those who have undergone extensive burns, fractures or major surgical operations). Reduced clearance of triglycerides and fatty acid has been recently shown to occur also in premature and small for gestational age babies.

It is, therefore, one object of the present invention to provide a pharmaceutical, triglyceride-comprising composition which allows the efficiency of exogenous triglycerides administered to patients for treatment of shock and trauma to be increased.

It is a further object of the present invention to provide a triglyceride-comprising composition suitable to minimize or prevent adverse metabolic reactions to exogenous triglycerides, such as the depletion of endogenous carnitine in the heart and other muscular tissues that can take place as a consequence of lipid pack administration.

In accordance with the present invention, there has now been discovered a pharmaceutical composition comprising a therapeutically effective amount of triglycerides, an amount of carnitine or a pharmaceutically acceptable salt thereof sufficient to enhance free fatty acid oxidation, and a pharmaceutically acceptable carrier therefor.

It has been found that exogenous carnitine enhances the efficiency of triglyceride administration, because carnitine increases the oxidation rate of free fatty acids derived from exogenous triglycerides parenterally administered to patients for treatment of shock and trauma.

It has in fact been found that exogenous carnitine is suitable for re-activating the mitochondrial respiration processes because it supplies energy-releasing material (i.e. the acyl groups) which has direct access to the Krebs cycle, and allows the passage of the long chain fatty acids through the mitochondrial membrane to be resumed, this making possible the beta-oxidation processes to get started again.

It has furthermore been found that co-administration of exogenous carnitine and exogenous triglycerides is suitable to counterbalance or prevent the carnitine depletion in the muscular tissues, particularly in the myocardium, which can be brought about by the administration of lipid packs to patients in need thereof for the treatment of shock and trauma.

DESCRIPTION OF THE PREFERRED EMBODIMENT

It has been found that a particularly suitable composition for the total parenteral nutrition in accordance with the present invention comprises:

| | |
|---|---|
| soybean oil | 50–200 g/l |
| glycerine | 22–26 g/l |
| egg yolk phospholipids (ovolecithin) | 10.5–12.5 g/l |
| carnitine or pharmaceutically acceptable salt thereof | 5–25 g/l |
| sodium hydroxide | sufficient to adjust the pH of the composition to 5.5–9.0 |
| distilled water | balance to 1 liter. |

The composition thus obtained is an isotonic intravenous emulsion having an osmolarity of from about 250 to 330 milliosmoles/kg of distilled water.

The desired daily dosage will be determined in accordance with standard usage, a daily dosage of 500 ml being generally sufficient.

A suitable mode of treating patients in need of total parenteral nutrition is to administer first the above specified emulsion and to continue carnitine administration for a total of 12 to 24 hours. This will ensure that sufficient carnitine is present to maintain high serum levels to increase triglyceride utilization and counterbalance any adverse metabolic effects of the triglycerides. Carnitine administration may be, therefore, started by intravenous perfusion and then continue by the oral or parenteral route.

As known, carnitine contains an asimmetric atom and consequently exists in two stereoisomers. Either the racemate or the isolated isomers can be conveniently used in the method of the present invention, although it appears that the L-isomer is more active, while the D-isomer is slightly more toxic. Thus, the $LD_{50}$ in rats and mice assessed for various routes of administration according to the Litchfield and Wilcoxon method is as shown in the following Table A. (Litchfield, J. T., and Wilcoxon, F., J. Pharm. Exptl. Therap. 96, 99. 1949).

TABLE A

| product | animal | route | $LD_{50}$(mg/kg) |
|---|---|---|---|
| D,L-carnitine | rat | i.v. | 995 |
| D-carnitine | " | sc | 10,000 |
| D,L-carnitine | mouse | i.v. | 610 |
| D,L-carnitine | " | sc | 6,000 |
| D-carnitine | " | sc | 5,400 |
| L-carnitine | " | sc | 7,000 |

The dose of carnitine which is administered will be determined by the attending physician having regard to the age, weight and condition of the patient, using sound professional judgement. Although effective utilization of exogenous glycerides can be noticed at doses as low as from 30 to 50 mg/kg of body weight daily, a dose of from about 150 to about 200 mg/kg of body weight daily is preferred. Should it be deemed necessary, larger doses can be safely administered, because of the extremely low toxicity of carnitine.

Some clinical studies are briefly summarized hereinbelow.

CASE 1

A 63 year old female, patient was hospitalized with duodenocutanous and colocutaneous fistulas; the fistulas had appeared 20 days earlier, after cholecystectomy and plastic repair of papilla (through duodenotomy) which had been complicated by post-surgical occlusion, which had required resection of the small bowel and right colon (with jejuno-colonic anastomosis).

Physical examination showed that general conditions were quite satisfactory; the patient had no fever; the entercutaneous fistulas on the abdominal wall were surrounded by areas of mild dermatitis.

Total output from the fistulas was about 600 ml per day. Nothing was allowed via the oral route; parenteral nutrition started according to the following schedule: 3000 ml daily of solutions containing amino acids, glucose and electrolyte, whose nitrogen/calories intake ratio was 1:140; 500 ml of 10% lipid solution with 1.4% carnitine was administered on alternate days.

Forty-five days later, while main haematological and biochemical parameters were still quite normal, the abdominal wall fistulas had closed spontaneously. The patient was discharged a few days later: oral feedings had been successfully reinstituted and nutritional function was regulard.

CASE 2

A 55 year old male patient, was hospitalized because of symptoms of acute pancreatitis which appeared two days previously. Upon physical examination, there was slight fever (37.8 C.°), epigastric tenderness and abdominal distention; slight muscular resistance was appreciable over the upper abdomen. The patient appeared to be mildly dehydratated; blood glucose was 208 mg%ml BUN 50 mg%ml, serum creatinine 7.7 mg%ml, serum diastasis activity 530 U/ml (normal range: 0 to 80).

A naso-gastric tube was inserted, and a catheter was placed in right atrium, to monitor central venous pressure. Parenteral nutrition was started via the peripheral route, according to the "protein sparing" schedule: 100 g of amino acids, elecrolytes, and a total amount of 5000 ml of daily fluids. A few days later, serum diastasis decreased to normal values, serum glucose was 90 to 130 mg%ml, BUN 15 to 35 gm%ml, creatinnine 0.7 to 1.2 mg%ml, triglycerides 80 to 120 mg%ml, and Ketone bodies were found in the urine; nitrogen balance is quite near to 0 (−6, −4). He had lost 10 kg during 15 days. Parenteral treatment was now changed by adding a 20% lipid solution with 2.1% carnitine (500 ml on alternate days, by the peripheral route, for 15 days). This treatment was continued until the patient had almost regained the body weight he had upon admission.

During the second part of treatment, we observed a positive nitrogen balance and increasing values of serum triglycerides; no other significant change was found in the main haematological and biochemical parameters. The patient recovered completly from pancreatitis and underwent cholecystectomy due to cholelithiasis.

CASE 3

A 44 year old female patient, was hospitalized in a severe state of sepsis caused by suppuration of pancreatic pseudocyst, which had already been treated by surgical drainage; 30 days before, in the immediate post partum period, the patient had had a sever episode of pancreatitis. Upon phisical examination, patient was in a febrile state: shivering and daily elevations of temperature (40° C.) were observed. A radiographic study was performed, injecting contrast material using the drainage tube: a little abscess cavity was evident, with several minor irregular branches which stretch towards the upper left quadrant of the abdomen.

Another surgical operation was required, in order to obtain satisfactory drainage of the cavity. Antibiotic therapy was started. The patient began total parenteral nutrition according to the following schedule: 40% glucose solution, 5% amino acid solution, electrolytes, 20% lipid solution with 2.5% carnitine. Lipids were administered by the peripheral route, 500 ml on alternate days.

The patient was digitalized, and cardiac output rose from 3.2 l/min/mq to 3.8 l/min/mq; oxygen consumption was 150-170 ml/min/mq. On the following days, several episodes of haemodynamic failure were observed, and polyuria appeared; episodes of shivering and fever were treated by antibiotic therapy. Parenteral nutrition was adjusted so that nitrogen/caloric intake ration did not exceed 1/120. Fourteen days later, general conditions had improved, fever disappeared, and oral feeding was reinstituted, (elementary diet).

What is claimed is:

1. In the method of increasing in a human the level of nutritional fatty acids selected from the group consisting of oleic acid, linolic acid, palmitic acid, stearic acid and linolenic acid by intravenously administering one or more in vivo hydrolysable triglycerides of said fatty acid to a human, the improvement which comprises simultaneously administering a quantity of carnitine sufficient to enhance the in vivo oxidation of said fatty acids.

2. The method of claim 1 wherein the carnitine is L-carnitine.

3. The method of claim 1 wherein the amount of carnitine administered is sufficient to supply from about 150 to about 200 mg/kg of body weight per day.

4. The method of claim 1 wherein a composition comprising from 50 to 20 g/L of triglycerides and from 5 to 25 g/L of carnitine is administered.

5. The method of claim 4 wherein the composition administered also includes from 22 to 26 g/L of glycerine and from 10.5 to 12.5 g of phospholipids and has a final pH of from 5.5 to 9.0.

6. An aqueous intravenous pharmaceutical composition for increasing in the body of a receipient thereof the level of nutritional fatty acids selected from the group consisting of oleic acid, linolic acid, palmitic acid, stearic acid and linolenic acid, said composition comprising a quantity of one or more triglycerides of said fatty acids sufficient upon in vivo hydrolysis to afford a nutritionally effective amount of said fatty acid, and an amount of carnitine or a pharmaceutically acceptable salt thereof sufficient to enhance the in vivo oxidation of said fatty acids.

7. A composition according to claim 6 wherein said carnitine is L-carnitine.

8. A composition according to claim 6 wherein the amount of carnitine is sufficient to supply from about 150 to about 200 mg/kg of body weight of the receipient per day.

9. A composition according to claim 6 wherein said triglycerides are those of soybean oil.

10. A composition according to claim 6 wherein said triglycerides are present in an amount of from 50 to 200 g/L of composition and said carnitine is present in an amount from 5 to 25 g/L of composition.

11. A composition according to claim 10 further including from 22 to 26 g of glycerine/L of composition, from 10.5 to 12.5 g of phospholipids/L of composition and having a final pH of from 5.5 to 9.0.

* * * * *